United States Patent [19]
Enei et al.

[11] 3,960,660
[45] June 1, 1976

[54] METHOD OF PRODUCING GUANOSINE BY FERMENTATION
[75] Inventors: Hitoshi Enei, Zushi; Katsuaki Sato, Kawasaki; Yoshio Hirose, Fujisawa, all of Japan
[73] Assignee: Ajinomoto Co., Inc., Tokyo, Japan
[22] Filed: Mar. 27, 1975
[21] Appl. No.: 562,402

[30] Foreign Application Priority Data
Mar. 30, 1974  Japan............................49-36371

[52] U.S. Cl............................................... 195/28 N
[51] Int. Cl.$^2$........................................ C12D 13/06
[58] Field of Search................................... 195/28 N

[56] References Cited
UNITED STATES PATENTS
3,575,809   4/1971   Shiro et al. ........................ 195/28 N

*Primary Examiner*—Alvin E. Tanenholtz
*Attorney, Agent, or Firm*—Cooper, Dunham, Clark, Griffin & Moran

[57] ABSTRACT

Production of guanosine by fermentation with a Bacillus mutant requiring adenine for growth and resistant to psicofuranine or decoyinine.

4 Claims, No Drawings

METHOD OF PRODUCING GUANOSINE BY FERMENTATION

This invention relates to methods of producing guanosine by fermentation.

Guanosine is widely employed for producing the sodium salt of guanosine 5'-monophosphate which is useful as a seasoning agent. It is known that mutants of Bacillus subtilis resistant to 8-azaguanine and requiring adenine for growth produce guanosine in the culture medium in which it grows (J. Gen. Appl. Microbiol., 15, 399–411 (1969)).

It has now been found that much greater yields of guanosine are produced, compared with known methods, by culturing, in a culture medium, a mutant of Bacillus which is resistant to psicofuranine or decoyinine, and which requires adenine for growth.

The mutants used in the process are derived from the parent strains by exposure to mutagenic doses of ionizing radiation (ultra-violet lights, X-rays, gamma-rays), or to chemical agents (sodium nitrate, N-methyl-N'-nitro-N-nitrosoguanidine, diethyl sulfate), and by screening the treated parent strains for mutants having the desired properties. Adenine-requiring mutants are isolated by the replication method, and mutants resistant to psicofuranine or decoyinine are identified by their ability of growing vigorously on otherwise conventional media containing enough of the compounds to suppress growth of the parent strains.

Resistance is determined by comparing the relative growth of the mutant in the presence of the compounds with that of parent strain, relative growth being the ratio of growth on a medium containing the compounds to growth on a medium free from the compounds.

Mutants which are also resistant to 8-azaguanine usually produce increased quantities of guanosine.

The presently preferred guanosine producing mutants are:

Bacillus subtilis AJ 3727 (FERM-P 2540) (resistant to decoyinine)

Bacillus subtilis AJ 3728 (FERM-P 2541) (resistant to 8-azaguanine, decoyinine)

Bacillus subtilis AJ 3729 (FERM-P 2542) (resistant to psicofuranine)

Bacillus subtilis AJ 3730 (FERM-P 2543) (resistant to 8-azaguanine, psicofuranine)

Microorganisms identified by FERM-P numbers are available from the Fermentation Research Institute of the Agency of Industrial Science and Technology, Chiba-shi, Chiba-ken, Japan.

The culture media in which the mutants of the invention produce guanosine are largely conventional. They must contain sources of assimilable carbon and nitrogen and adenine, and should further contain inorganic ions and minor organic nutrients. Suitable carbon sources include glucose, fructose, sucrose, starch hydrolyzate and molasses. Nitrogen may be derived from nitrates, ammonium salts, ammonium hydroxide, urea, and like inorganic and organic compounds.

Aerobic conditions are maintained by aeration and/or agitation, and pH is held between 5 and 9 for optimum yields. When ammonia is used for pH control, it may also serve as a nitrogen source. The guanosine concentration in the broth reaches its maximum within 2 to 7 days if the fermentation is carried out at 24° to 37°C.

The guanosine accumulated in the fermentation broth can be recovered by conventional methods, such as removing cells by filtration or centrifuging, passing the broth over an ion exchange resin.

The following non-limiting examples are given by way of illustration only:

EXAMPLE 1

Resistance of the mutants to the compounds listed in the Tables was tested as follows:

An aqueous medium was prepared to contain, per deciliter, 0.02 g $MgSO_4 \cdot 7H_2O$, 0.05 g. sodium citrate, 0.1 g L-glutamic acid, 2.5 g glucose, 0.5 g $NH_4Cl$, 0.4 g $KH_2PO_4$, 1 mg $FeSO_4 \cdot 7H_2O$, 1 mg $MnSO_4 \cdot 4H_2O$, 100 $\mu$g vitamin $B_1$, 10 mg adenine and 0.2 g casein-hydrolyzate (pH 7.0). The aqueous medium was implemented with each of the compounds listed in Tables 1 and 2, and placed (total volume 3 ml) in test tubes. Each tube was inoculated after sterilization with 0.05 ml of a cell suspension containing $10^6$ cells/ml, and shaken at 34°C for 24 hours. Growth was determined by measuring the turbidity of the culture broth. Results are shown in Tables 1 and 2.

EXAMPLE 2

Each microorganism listed in Table 3 was cultured with shaking at 34°C for 16 hours in an aqueous culture medium containing 2 g/dl glucose, 0.5 g/dl yeast extract, 0.1 g/dl NaCl, 20 mg/dl adenine, 4 ml/dl soy protein-acid hydrolyzate ("MIEKI"), 0.02 g/dl $KH_2PO_4$ and 0.04 g/dl $MgSO_4 \cdot 7H_2O$ of pH 7.5.

An aqueous fermentation medium was prepared to contain, per deciliter, 8 g glucose, 1.5 g $NH_4NO_3$, 0.02 g $KH_2PO_4$, 0.04 g $MgSO_4 \cdot 7H_2O$, 0.2 mg ferrous ion, 0.2 mg manganese ion, 0.2 g $CaCl_2 \cdot 2H_2O$, 0.14 gRNA (separated from yeast), 4 ml soy protein-acid hydrolyzate and 3 g $CaCO_3$ (separately sterilized), adjusted to pH 7.0, and sterilized with steam.

20 ml Batches of the fermentation medium in 500 ml flasks were each inoculated with 1 ml of the previously prepared seed cultures.

Fermentation was carried out at 34°C with shaking for 72 hours. The amount of guanosine in each fermentation broth was determined by paper-chromatography. The results are shown in Table 3.

1.0 Liter of the fermentation broth utilized with AJ 3728 was prepared in the manner described above. Cells were separated from the broth by filtration, and thereafter guanosine was isolated with an anion exchange resin. 8.2 g of crude guanosine crystalline were precipitated by adding acetone to the eluate.

Table 1

| Decoyinine $\gamma$/ml | Relative growth (%) | | |
|---|---|---|---|
| | AJ 3483 | AJ 3727 | AJ 3728 |
| 0 | 100 | 100 | 100 |
| 100 | 78 | 88 | 92 |
| 500 | 0 | 60 | 74 |
| 1,000 | 0 | 24 | 38 |
| 2,000 | 0 | 0 | 5 |

Table 2

| Psicofuranine $\gamma$/ml | Relative growth (%) | | |
|---|---|---|---|
| | AJ 3483 | AJ 3729 | AJ 3730 |
| 0 | 100 | 100 | 100 |
| 100 | 95 | 95 | 95 |

Table 2-continued

| Psicofuramine γ/ml | Relative growth (%) | | |
|---|---|---|---|
| | AJ 3483 | AJ 3729 | AJ 3730 |
| 500 | 28 | 75 | 80 |
| 1,000 | 0 | 48 | 62 |
| 1,500 | 0 | 24 | 32 |
| 2,000 | 0 | 10 | 8 |

Table 3

| Microorganism | Guanosine accumulated (g/l) |
|---|---|
| Bacillus subtilis AJ 3483 | 1.8 |
| Bacillus subtilis AJ 3727 | 7.5 |
| Bacillus subtilis AJ 3728 | 10.8 |
| Bacillus subtilis AJ 3729 | 8.8 |
| Bacillus subtilis AJ 3730 | 10.6 |

Bacillus subtilis AJ 3483 is an adenine-requiring and guanosine-producing mutant from which the mutants of this invention were induced.

What is claimed is:

1. A method for producing guanosine, which comprises culturing a guanosine-producing mutant of the genus Bacillus, which requires adenine for growth and is resistant to 1,000γ/ml of psicofuramine or 500γ/ml of decoyinine under aerobic conditions in an aqueous culture medium until guanosine accumulates in the medium, and recovering accumulated guanosine from culture medium.

2. A method as set forth in claim 1 in which the mutant is characterized as resistant to 8-azaguanine.

3. A method as set forth in claim 1 in which the mutant is of the strain Bacillus subtilis.

4. A method as set forth in claim 1 in which the mutant is Bacillus subtilis FERM-P 2540, Bacillus subtilis FERM-P 2541, Bacillus subtilis FERM-P 2542, Bacillus subtilis FERM-P 2543.

* * * * *